United States Patent [19]

Eisenhart et al.

[11] Patent Number: 5,281,654
[45] Date of Patent: Jan. 25, 1994

[54] POLYURETHANE MIXTURE

[75] Inventors: Eric K. Eisenhart, Doylestown, Pa.; Paul R. Howard, Tulsa, Okla.; Rodney L. Randow, Jeffersonville, Pa.; Rafael G. Aviles, Harleysville, Pa.

[73] Assignee: Rohm and Haas Company, Philadelphia, Pa.

[21] Appl. No.: 4,378

[22] Filed: Jan. 14, 1993

[51] Int. Cl.$^5$ .............................................. C08L 75/04
[52] U.S. Cl. ................................. 524/500; 524/590; 525/457; 525/458; 528/49; 528/76
[58] Field of Search ................ 524/500, 590; 525/457, 525/458; 528/49, 76

[56] References Cited

U.S. PATENT DOCUMENTS

| | | | |
|---|---|---|---|
| 3,770,684 | 11/1973 | Singer et al. | 528/60 |
| 4,079,028 | 3/1978 | Emmons et al. | 524/700 |
| 4,155,892 | 5/1979 | Emmons et al. | 524/700 |
| 4,426,485 | 1/1984 | Hoy et al. | 524/700 |
| 4,496,708 | 1/1985 | Dehm et al. | 524/700 |
| 4,499,233 | 2/1985 | Tetenbaum et al. | 528/76 |
| 4,507,426 | 3/1985 | Blake, Jr. | 524/700 |
| 5,023,309 | 6/1991 | Kruse et al. | 524/102 |

FOREIGN PATENT DOCUMENTS 1069735 5/1967 Fed. Rep. of Germany.

Primary Examiner—Maurice J. Welsh
Attorney, Agent, or Firm—James G. Vouros

[57] ABSTRACT

This invention is directed to a polyurethane mixture. More particularly, there is provided a mixture polyurethanes comprising a first polyurethane with at least two end groups, where each end group comprises a terminal isocyanate and a polyether; a second polyurethane with at least two end groups, where each end group comprises a terminal isocyanate group and a non-functional group; and a third polyurethane with at least two end groups, where one end group comprises a terminal isocyanate and a polyether and one other end group comprises a terminal isocyanate and a non-functional group. A method for improving the sag resistance of an aqueous composition is also provided. This method permits the formulation of aqueous compositions which resist the tendency to sag. The polyurethane mixture of this invention is useful for thickening aqueous compositions such as paints, coatings, cosmetics, personal care items, hair shampoos and conditioners, cleaners, and the like.

23 Claims, No Drawings

POLYURETHANE MIXTURE

FIELD OF THE INVENTION

This invention relates to a polyurethane mixture. In particular, this invention is related to a polyurethane mixture useful for thickening aqueous compositions.

BACKGROUND OF THE INVENTION

Thickeners are useful for decorative and protective coatings, paper coatings, cosmetics and personal care items, detergents, pharmaceutical, adhesives and sealants, agricultural formulations, petroleum drilling fluids, and the like.

Thickeners have several roles in aqueous systems. They increase viscosity and maintain viscosity at required levels under specified processing conditions and end use situations. In latex decorative coatings, for example, the thickener may provide improved stability, pigment suspension, and application properties. In cosmetics and personal care items, the thickener improves body, smoothness and silkiness, making the product more aesthetically pleasing. In petroleum drilling fluids, the thickener improves the suspension of the cuttings, increasing the efficiency with which they can be removed.

Many thickeners, both natural and synthetic, are known. Natural thickeners, for example, include casein, alginates, gum tragacanth, and modified cellulose, including methyl cellulose, hydroxyethyl cellulose, hydroxypropyl cellulose, and carbomethoxy cellulose. These natural products vary in their thickening efficiency, and generally provide poor flow and leveling properties. They are also subject to microbial attack which requires the additional presence of antimicrobial agents. Synthetic thickeners include various acrylic polymers and maleic anhydride copolymers. Some of these are found to be pH dependent, others are hydrolytically unstable, and others are sensitive to various components normally found in aqueous coatings.

One type of synthetic thickener is a polyurethane. U.S. Pat. No. 4,079,028 discloses polyurethane thickeners having at least three hydrophobic groups, such as hydrophobic isocyanate groups, interconnected by hydrophilic polyether groups. These polyurethanes have terminal hydrophobic groups.

Aqueous coating compositions thickened with polyurethane thickeners have good flow and leveling. "Leveling" as used herein, refers to the degree to which a coating flows out after application so as to obliterate any surface irregularities such as for example, brush marks, "orange peel", peaks, or craters, which have been produced by the mechanical process of applying a coating. Thus, aqueous coatings thickened with polyurethane thickeners have a desirable, smooth appearance when dried.

Despite these advantages, aqueous coatings thickened with polyurethane thickeners require improvement in their resistance to sagging. "Sagging", is the downward movement of a coating on a vertical surface between the time of application and setting, resulting in an uneven coating having a thick bottom edge. The resulting sag is usually restricted to a local area of a vertical surface and may have the characteristic appearance of a draped curtain. Sagging is aesthetically undesirable. In addition, coatings which resist the tendency to sag will not easily drip off a paint brush or a paint roller and will not easily drip off a horizontal surface, such as for example, a ceiling.

There is a need for a polyurethane thickener that possesses good thickening efficiency and desirable sag resistance.

According to a first aspect of the present invention, there is provided a mixture of polyurethanes comprising a first polyurethane with at least two end groups, where each end group comprises a terminal isocyanate and a polyether; a second polyurethane with at least two end groups, where each end group comprises a terminal isocyanate group and a non-functional group; and a third polyurethane with at least two end groups, where one end group comprises a terminal isocyanate and a polyether and one other end group comprises a terminal isocyanate and a non-functional group.

A second aspect of the invention is an aqueous composition comprising from 0.005 to 20 percent by weight of this polyurethane mixture.

A third aspect of the present invention is directed to a method of improving the sag resistance of an aqueous composition by adding this polyurethane mixture at a concentration of from 0.005 to 20 percent by weight of the aqueous composition.

The polyurethane mixture of this invention is particularly advantageous for use in latex coating compositions, especially in paints. While it is useful for increasing the viscosity of an aqueous composition, the most important advantage is the sag resistance it imparts. Aqueous compositions thickened with the polyurethane mixture of this invention are structured and solid-like, characteristic of a gel. The gel structure generated by the polyurethane thickener is desirable because aqueous compositions with gel structure resist the tendency to sag. In addition, aqueous compositions with gel structure do not drip easily off a paint brush or paint roller. A further advantage of the improved polyurethane mixture of the present invention is that it is resistant to microbial attack and incorporates easily in aqueous compositions. In addition, the polyurethane of this invention is also advantageous because it can be used as a cothickener with other thickeners to obtain an aqueous composition which does not sag and has a desirable balance of other properties, such as for example, flow and leveling.

This invention is directed to a mixture of polyurethanes. Each of the polyurethanes in the mixture may be present in an amount ranging from about 5 to about 90 mole percent. More preferably, the first polyurethane is present in the mixture in an amount ranging from about 8.3 to about 75 mole percent, the second polyurethane is present in the mixture in an amount ranging from about 8.3 to about 75 mole percent, and the third polyurethane is present in the mixture in an amount ranging from about 16.7 to about 83.4 mole percent. Even more preferably, the first polyurethane is present in the mixture in an amount ranging from about 8.3 to about 25 mole percent, the second polyurethane is present in the mixture in an amount ranging from about 25 to about 75 mole percent, and the third polyurethane is present in the mixture in an amount ranging from about 16.7 to about 50 mole percent. Most preferably, the first polyurethane is present in the mixture in an amount ranging from about 12.5 to about 25 mole percent, the second polyurethane is present in the mixture in an amount ranging from about 25 to about 62.5 mole percent, and the third polyurethane is present in the mixture in an amount ranging from about 25 to about 50 mole percent.

Generally, the polyurethanes in the mixture are characterized by their end groups. One possible end group is the reaction product of a terminal isocyanate and a polyether alcohol, hereinafter referred to as the "polyether end group." Another possible end group is the reaction product of a terminal isocyanate and a reactant, so that this end group cannot further polymerize or participate in any further reactions once this reaction has occurred, hereinafter referred to as the "non-functional end group." The end groups on the polyurethane may be in any sequence and do not exclude the possibility that the polyurethane contains additional end groups such as being branched or star-shaped. For any end group that is the reaction product of a polyether alcohol and a terminal isocyanate, the polyether alcohol must have only one terminal hydroxyl moiety which can react with the terminal isocyanate so that the polyether end group cannot further polymerize or react after this reaction has occurred.

The polyether alcohol includes alkyl and aryl polyether alcohols. These alcohols may be straight or branched ($C_1$-$C_{22}$) alkanol/ethylene oxide and alkyl phenol/ethylene oxide adducts, such as for example, methanol, ethanol, propanol, lauryl alcohol, t-octylphenol or nonylphenol ethylene oxide adducts containing 1-250 ethylene oxide groups. In addition, the polyether alcohol may also include alkanol/propylene oxide and alkyl phenol/propylene oxide adducts containing 1-250 propylene oxide groups. More preferred polyether alcohols in this invention include polyethylene glycol methyl ether and polypropylene glycol methyl ether. Most preferred polyether alcohols are polyethylene glycol methyl ethers with 15-50 ethylene oxide groups.

The non-functional end group is derived from a reactant such as an alcohol, amine, acid, mercaptan, and the like. It is preferred that the reactant is monofunctional in that it only has one group containing a hydrogen atom that can react with the terminal isocyanate group such as, for example, a monofunctional alcohol, monofunctional amine, monofunctional acid, or monofunctional mercaptan.

The monofunctional alcohol may include the alkyl alcohols ($C_1$-$C_{40}$) such as methanol, ethanol, octanol, dodecanol, octadecanol, tetradecanol, hexadecanol, and cyclohexanol, and the phenolics such as, for example, phenol, cresol, octylphenol, nonyl and dodecylphenol. More preferred alcohols include the $C_{14}$-$C_{20}$ alkyl alcohols, and a most preferred alcohol is 1-octadecanol.

The monofunctional amine may include both primary and secondary aliphatic, cycloaliphatic or aromatic amines such as the straight or branched chain alkyl amines, or mixtures thereof, containing about 1-20 carbon atoms in the alkyl group. Suitable amines include for example, n- and t-octyl amine, n-dodecyl amines, $C_{12}$-$C_{14}$ or $C_{18}$-$C_{20}$ n-alkyl and t-alkyl amine mixtures, and secondary amines such as N,N-dibenzyl amine, N,N-dicyclohexyl amine and N,N-dibenzyl amine.

The monofunctional acid may include, for example: $C_8$-$C_{22}$ alkyl carboxylic acids, such as, for example, octanoic acid, decanoic acid, tetradecanoic acid, hexadecanoic acid, octadecanoic acid (stearic acid), eicosonoic acid, docosonoic acid; naturally occurring mixtures of acids, such as cocoa acids, tallow acids, rapeseed acids and the hydrogenated forms of these acids; aromatic acids, such as benzoic acid and napthenoic acids; alkyl substituted aromatic acids, such as octylbenzoic acid and dodecylbenzoic acid; alicyclic acids, such as cyclopentane carboxylic acid, cyclohexanecarboxylic acid, and cyclooctanecarboxylic acid; and alkoxypropyl acids derived from the Michael addition of alcohols of acrylic acid, such as 3-octyloxypropanoic acid, 3-dodecyloxypropanoic acid and 3-octadecyloxypropanoic acid.

The monofunctional mercaptan may include $C_1$-$C_{30}$ mercaptans such as, for example, octyl mercaptan, decylmercaptan, dodecylmercaptan, tetradecylmercaptan, hexadecylmercaptan, octadecylmercaptan and the like.

The processes for the preparation of the polyurethane mixtures in this invention are well known and are illustrated in U.S. Pat. No. 4,079,028. The polyurethanes in the mixture can be prepared individually and then blended. It is preferred to prepare the polyurethane mixture in a one step process whereby all three polyurethanes are prepared simultaneously in the same reactor. The polyurethane mixtures are the reaction products of an organic diisocyanate; polyol, such as, for example, polyethylene glycol, polyether alcohol; and at least one reactant such as an alcohol, amine, acid, or mercaptan. The molar ratio of polyol to diisocyanate ranges from 1:1.01 to 1:5, preferably from 1:1.01 to 1:3. The moles of polyether alcohol and reactant must be at least two times greater than the difference between the moles of diisocyanate and polyol. The molar ratio of polyether alcohol to the reactant is from 10:1 to about 1:10, and more preferably from 1:1 to 1:5. The percent of each type of polyurethane in the mixture may be varied by changing the molar ratio of the polyether alcohol and reactant. A convenient reaction temperature is about 40° C. to about 150° C., preferably from about 60° C. to about 130° C.

It is preferable that the weight average molecular weight, Mw, of the polyether alcohol is greater than 500. It is also preferable that the weight average molecular weight, Mw, of the reactant, such as, for example, the monofunctional alcohol, monofunctional amine, monofunctional mercaptan, monofunctional acid, and the like, is less than 500.

The polyurethane mixture may be incorporated into aqueous compositions in amounts ranging from 0.005% to 20%, preferably from 0.01% to 10% and most preferably from 0.05% to 2.0% by weight of the aqueous composition. The polyurethane mixture may be mixed into the aqueous composition using conventional mixing equipment such as, for example, high speed dispersers, ball mills, sand mills, pebble mills, paddle mixers, and other such mixing equipment. The polyurethane mixture may be in the form of a dry powder, a premixed aqueous solution or a slurry or a solution in a water compatible solvent. In this regard, a solvent may be selected to prepare the polyurethane mixture so that it may be directly mixed into the aqueous composition. Of course, the composition may normally contain other known ingredients, such as, for example, pigments, surfactants, defoamers, preservatives, and the like, in known combinations and amounts depending on the particular end use.

Typical aqueous compositions which may include the polyurethane mixture of the present invention are paints, coatings, synthetic plaster, cosmetics, personal care items such as, for example, shampoos, hair conditioners, hand lotions, hand creams, astringents, depilatories, and antiperspirants, adhesives, sealants, inks, drilling fluids, packer fluids, topical pharmaceutical, cleaners, fabric softeners, pesticidal and agricultural compositions, and any other aqueous compositions requiring thickening. Usually these latex coating compositions contain added pigments, fillers and extenders such as, for example, titanium dioxide, barium sulfate, calcium carbonate, clays, mica, talc, silica, and the like.

Aqueous compositions thickened with the polyurethane mixture of this invention resist the tendency to sag. The sag resistance of a paint is measured as follows.

Measurement of Sag Resistance

The sag resistance is measured using an anti-sag bar (supplied by the Leneta Company). The bar has notches of varying thickness, from 4 to 24 mils (one thousandth of an inch). The clearances on the bar in mils are identified by a number next to each notch on the bar. A sealed chart is marked with a water-soluble pen line drawn perpendicular to the direction of the intended path of the anti-sag bar. The anti-sag bar is placed at the top end of the sealed chart. Each paint is thoroughly mixed by hand. Each paint is drawn up through a syringe without a needle tip. The needle tip is then affixed to the end of the syringe. The paint is applied by shooting the paint through the needle to the chart in front of the anti-sag bar. The anti-sag bar is then used to cast a film of the paint. The chart is then suspended vertically such that paint stripes of varying thickness are vertical, and the water-soluble marker line is horizontal. As the wet paint dries, the water-soluble marker ink mixes with the paint and moves down the chart as the paint sags. When the paint dries, the sag resistance is determined as the greatest notch clearance on the bar which sagged the ink mark less 0.5 mm. A sag rating of 4 mils indicates very poor sag resistance and a rating of 24 mils or greater indicates excellent sag resistance.

Aqueous compositions thickened with the polyurethane mixture of this invention are structured and have gel strength. The gel strength of a paint is measured as follows.

Measurement of Gel Strength

Gel strength is measured with an instrument called an ICI gel strength tester, or ICI rotothinner. The paint is left undisturbed in the can for 3 days. The ICI gel strength tester is a paddle viscometer. The paddle is lowered into the paint, and the paint is turned at a constant speed. The force (grams/centimeter) needed to turn the paint against the paddle is measured. The stress rises to a high and then ebbs back to a lower level as the thixotropic structure breaks down. By "thixotropic", we mean flow behavior in which the viscosity is reduced by agitation or stirring.

EXAMPLE 1

Preparation of Polyurethane Mixture

To a one liter flask was added 195 grams of a polyethylene glycol of approximate molecular weight 8,000, 325 grams of toluene, and 0.2 grams of dibutyltin dilaurate. The mixture was azeotropically dried by refluxing the mixture and collecting any water in a Dean-Stark trap, cooled to 80° C., and 8.2 grams of methylene bis(4-cyclohexyl isocyanate) was added. After 2.5 hours, a mixture of 4.7 grams of 1-octadecanol and 11.5 grams of a polyethylene glycol methyl ether of approximate molecular weight 2,000 was added. The mixture was held at 80° C. for 4 hours and then cooled. The solid product was isolated by evaporation of the toluene.

EXAMPLE 2

The procedure of Example 1 was repeated except that after 2.5 hours, a mixture of 3.1 grams of 1-octadecanol and 23.0 grams of the polyethylene glycol methyl ether was added.

EXAMPLE 3

To a one liter flask was added 240 grams of a polyethylene glycol of approximate molecular weight 8,000, 400 grams of toluene, and 0.2 grams of dibutyltin dilaurate. The mixture was azeotropically dried by refluxing the mixture and collecting any water in a Dean-Stark trap, cooled to 80° C., and 10.1 grams of methylene bis(4-cyclohexyl isocyanate) was added. After 3 hours, a mixture of 3.8 grams of 1-octadecanol and 33.0 grams of a 50 weight percent solution of a polypropylene glycol methyl ether of approximate molecular weight 1,180 in toluene was added. The mixture was then held at 80° C. for 3 hours. The mixture was then heated to 100° C. for 9 hours and then cooled. The solid product was isolated by evaporation of the toluene.

EXAMPLE 4

The procedure of Example 1 was repeated except that after 3 hours (instead of after 2.5 hours), a mixture of 2.7 grams of 1-decanol and 11.4 grams of the polyethylene glycol methyl ether was added. The mixture was held at 80° C. for 3 hours and then cooled. The solid product was isolated by evaporation of the toluene.

EXAMPLE 5

The procedure of Example 4 was repeated except that after 3 hours, a mixture of 3.2 grams of 1-dodecanol and 11.4 grams of polyethylene glycol methyl ether was added.

EXAMPLE 6

The procedure of Example 4 was repeated except that after 3 hours, a mixture of 3.7 grams of 1-tetradecanol and 11.4 grams of polyethylene glycol methyl ether was added.

EXAMPLE 7

The procedure of Example 4 was repeated except that after 3 hours, a mixture of 4.2 grams of 1-hexadecanol and 11.4 grams of polyethylene glycol methyl ether was added.

EXAMPLE 8

To a one liter flask was added 192 grams of a polyethylene glycol of molecular weight 8,000, 325 grams of toluene, and 0.2 grams of dibutyltin dilaurate. The mixture was azeotropically dried by refluxing the mixture and collecting any water in a Dean-Stark trap, cooled to 80° C., and 8.2 grams of methylene bis(4-cyclohexyl isocyanate) was added. After 2.5 hours, a mixture of 1.0 gram of 1-octadecanol and 37.4 grams of a polyethylene glycol methyl ether of approximate molecular weight 2,000 was added. The mixture was held at 80° C. for 4 hours and then cooled. The solid product was isolated by evaporation of the toluene.

EXAMPLE 9

The procedure of Example 8 was repeated except that after 2.5 hours, a mixture of 1.5 grams of 1- octadecanol and 33.6 grams of the polyethylene glycol methyl ether was added.

EXAMPLE 10

The procedure of Example 8 was repeated except that after 2.5 hours, a mixture of 4.5 grams of 1-octadecanol and 11.2 grams of the polyethylene glycol methyl ether was added.

EXAMPLE 11

The procedure of Example 8 was repeated except that after 2.5 hours, a mixture of 5.1 grams of 1-octadecanol and 7.6 grams of the polyethylene glycol methyl ether was added.

EXAMPLE 12

To a one liter flask was added 197.5 grams of a polyethylene glycol of approximate molecular weight 8,000, 331 grams of toluene, and 0.2 grams of dibutyltin dilaurate. The mixture was azeotropically dried by refluxing the mixture and collecting any water in a Dean-Stark trap, cooled to 80° C., and 7.4 grams of methylene bis(4-cyclohexyl isocyanate) was added. After 2.5 hours, a mixture of 3.4 grams of Unilin ® 425 (triacontanol) and 15.4 grams of a polyethylene glycol methyl ether of approximate molecular weight 2,000 was added. The mixture was held at 80° C. for 4 hours and then cooled. The solid product was isolated by evaporation of the toluene.

EXAMPLE 13

Paint Thickened with the Polyurethane Mixture

This example demonstrates the use of the polyurethane mixture of Example 1 for thickening a paint. A commercial polyurethane thickener which is not a mixture was also evaluated for comparison (Comparative A). The latex paint formulation used in this example was:

| INGREDIENT | AMOUNT (parts by weight) |
| --- | --- |
| Water | 106.7 |
| Hydrophilic acrylic dispersant | 11.5 |
| Propylene glycol | 25.0 |
| Defoamer | 2.0 |
| Titanium Dioxide | 250.0 |
| Clay | 100.0 |
| Clay | 5.0 |
| Acrylic Binder (60.5% solids) | 350.1 |
| Coalescent | 10.6 |
| Defoamer | 4.0 |
| Thickener/Water | 234.7 |

Each paint composition was thickened using a sufficient amount of thickener (on a dry weight basis) to give a low shear viscosity (as measured with a Krebs-modified Stormer Viscosity) of about 95 Krebs units (KU) after 2 days equilibration at room temperature. The sag resistance and ICI gel strength of the paints were measured and the results are shown in Table 1.

TABLE 1

| Thickener | Thickener (Dry Lbs/ 100 gal.) | KU | Sag Resistance (mils) | ICI Gel Strength (g/cm) |
| --- | --- | --- | --- | --- |
| Example 1 | 4.1 | 96 | 24 | 47 |
| Comparative A | 2.7 | 95 | 8 | 0 |

The results in Table 1 show that Example 1 generated greater sag resistance than Comparative A. In addition, Example 1 generated significant gel strength whereas Comparative A did not generate any gel strength.

EXAMPLE 14

Polyurethane as a Cothickener

The polyurethane mixture of Example 1 was blended with a commercial polyurethane thickener at dry weight ratios of 1/1, 1/3, and 1/6 (Example 1/Commercial Polyurethane). These thickeners were used to thicken a gloss paint formulation.

| INGREDIENT | AMOUNT (parts by weight) |
| --- | --- |
| Methyl Carbitol | 44.8 |
| Water | 10.0 |
| Hydrophilic Acrylic Dispersant (25%) | 7.8 |
| Surfactant | 1.8 |
| Defoamer | 2.0 |
| Titanium Dioxide | 195.0 |
| Acrylic Binder (42.5% solids) | 540.7 |
| Water | 107.9 |
| Coalescent | 34.6 |
| Defoamer | 2.0 |
| Thickener/Water | 50.2 |

Each paint composition was thickened using a sufficient amount of thickener (on a dry weight basis) to give an equilibrated low shear viscosity (as measured with a Krebs-modified Stormer Viscosity) of about 97 Krebs units (KU) after 2 days equilibration. The paints were evaluated for sag resistance and ICI gel strength as previously described. Leveling was determined using ASTM Standard Test Method for Leveling of Paints by Draw-Down Method (ASTM D-4062-88). The leveling rating scale was 1–10, with 10 indicating the best leveling and 1 indicating the worst leveling.

Gloss was measured on dried films of paint cast with a three mil Byrd applicator. The paint film was then allowed to dry for seven days at 77° F./50% R.H. Gloss was measured with a Glossgard II gloss meter. Values are reported for angles of incidence 20° and 60° from normal. The data are shown in Table 2.

TABLE 2

| Thickener* | Thickener Dry Lbs./ 100 gal. | KU | Leveling | Sag Resistance (mils) | ICI gel Strength (g/cm) | Gloss 20°/ 60° |
| --- | --- | --- | --- | --- | --- | --- |
| 1/1 Ratio | 1.4 | 95 | 5 | >24 | 60 | 43/81 |
| 1/3 Ratio | 2.0 | 98 | 9− | >24 | 30 | 42/81 |
| 1/6 Ratio | 2.4 | 99 | 9+ | 19 | 10 | 43/80 |

*Blends: Example 1 and Commercial Polyurethane (Dry Weight Ratio)

Table 2 shows that Example 1 polyurethane mixture can be blended with another commercial polyurethane thickener to obtain a desirable balance of leveling, sag resistance, and gloss.

EXAMPLE 15

Effect of Molar Ratio of Monofunctional Alcohol/Polyether Alcohol

Five polyurethane mixtures were made with a different molar ration of 1-octadecanol (reactant group) and polyethylene glycol methyl ether (polyether alcohol). These thickeners were formulated into the paint formulation from Example 13. Each paint composition was thickened using a sufficient amount of thickener (on a dry weight basis) to give an equilibrated KU viscosity of about 94 KU after 2 days equilibration. Sag resistance of these paints was measured as described in the specification.

TABLE 3

| Polyurethane Example Number | 1-Octadecanol/ Polyethylene Glycol Methyl Ether Molar Ratio | Thickener Dry Lbs/ 100 gals. | KU | Sag Resistance (mils) |
|---|---|---|---|---|
| 11 | 5/1 | 3.5 | 94 | >24 |
| 10 | 3/1 | 4.0 | 94 | >24 |
| 2 | 1/1 | 6.9 | 94 | >24 |
| 7 | 1/3 | 14.1 | 96 | 16 |
| 8 | 1/5 | 22.7 | 91 | 11 |

The table shows that both thickener efficiency and sag resistance balance changed with the 1-octadecanol/polyethylene glycol methyl ether ratio. Thickener efficiency is defined as the amount of thickener to reach the same viscosity (KU). The greater the amount of thickener required to reach a specified viscosity the lower was the thickening efficiency.

EXAMPLE 16

Effect of Chain Length of Monofunctional Alcohol (Reactant)

A series of polyurethane mixtures were made with different length monofunctional alkyl alcohols at a 3/1 molar ratio of alcohol to polyethylene glycol methyl ether. These samples were formulated into the paint formulation from Example 13. Each paint composition was thickened using a sufficient amount of thickener (on a dry weight basis) to give an equilibrated KU viscosity of about 94 KU after 2 days equilibration. The paints were evaluated for sag resistance as described in the specification. The results are shown in Table 4.

TABLE 4

| Example | Alkly (Cx) Alcohol Length | Thickener Dry Lbs./ 100 gal. | KU | Sag resistance (mils) |
|---|---|---|---|---|
| 4 | C10 | 4.0 | 94 | 7 |
| 5 | C12 | 3.0 | 94 | 10 |
| 6 | C14 | 2.9 | 93 | 12 |
| 7 | C16 | 3.5 | 95 | 20 |
| 10 | C18 | 4.0 | 94 | >24 |

Table 4 shows that increasing the length of the monofunctional alkyl alcohol increased sag resistance. The polyurethane mixture made with the $C_{18}$ alcohol (1-octadecanol) had the greatest sag resistance.

EXAMPLE 17

Polyether Alcohols

Polyurethane mixtures were made with a 1/1 molar ration of 1-octadecanol to each of two different polyether alcohols. The polyether alcohols were a polyethylene glycol methyl ether of approximate molecular weight 2,000 and a polypropylene glycol methyl ether of approximate molecular weight 1000. These samples were used to thicken the paint of the formulation given in Example 13. Each paint composition was thickened using a sufficient amount of thickener (on a dry weight basis) to give an equilibrated KU viscosity of about 95 KU after 2 days equilibration. Sag resistance and ICI gel strength were measured as described in the specification. The results are shown in Table 5.

TABLE 5

| Example | Polyether Alcohol | Thickener Dry Lbs/ 100 gal. | KU | Sag Resistance (mils) | ICI Gel Strength (g/cm) |
|---|---|---|---|---|---|
| 2 | Polyethylene Glycol Methyl Ether | 6.1 | 95 | Greater than 24 | 32 |
| 3 | Polypropylene Glycol Methyl Ether | 4.0 | 95 | Greater than 24 | 16 |

Table 5 shows that both polyethylene glycol methyl ether and polypropylene glycol methyl ether are useful for the polyether alcohol.

EXAMPLE 18

Use of Polyurethane in Cosmetic and Personal Care Applications a) Hair Conditioners A quaternary ammonium salt, such as, for example, Carsoquat ® 868P (dicetyldimethyl ammonium chloride, supplied by Lonza) is the active ingredient in hair conditioners. Hair conditioners are thickened to provide a desirable viscosity upon application. The thickener must be compatible with the quaternary ammonium salt.

A solution of 2% by weight solids of Carsoquat ® 868P (68% by weight solids) and 1% by weight solids of the polyurethane mixture of Example 1 was made by adding 5.88 grams of Carsoquat ® 868 and 10 grams of the polyurethane of Example 1 (20% by weight solids) to 184.12 grams of water. The solution was stirred at room temperature. A solution of 1% by weight solids of the polyurethane mixture of Example 1 was made by adding 10 grams of the polyurethane to 190 grams of water and stirring the solution until blended. The viscosities of these solutions were measured using a Brookfield LVT viscometer at 12 rpm. Table 6 shows the viscosities of these solutions.

TABLE 6

| Sample (% By Weight Solids) | Viscosity, cps (Spindle Number) |
|---|---|
| 2% Carsoquat ® 868P + 1% Example 1 | 16000 (2) |
| 1% Example 1 | 3820 (3) |

Table 6 shows that Example 1 was useful for thickening a 2% by weight solution of Carsoquat ® 868P. Example 1 was compatible with Carsoquat ® 868P in solution and did not separate on standing.

b) Dandruff Shampoos, Astringents, and Sunscreens containing Zinc Compounds

Dandruff shampoos may contain zinc pyrithione as the active ingredient. Astringents may contain zinc phenol as the active ingredient. Sunscreens may contain zinc oxide as the active ingredient. Shampoos, astringents, and sunscreens containing zinc compounds are thickened so the zinc does not separate and settle out of solution and to provide desired end-use viscosity.

A solution of 0.5% zinc and 2% by weight solids of the polyurethane mixture of Example 1 was made by adding 2.08 grams of zinc chloride and 20 grams of Example 1 (20% by weight solids) to 177.92 grams of water. The solution was stirred at room temperature. A solution of 0.5% by weight of zinc and 2% by weight solids of Comparative A (25% by weight solids) was made by adding 2.08 grams of zinc chloride and 16 grams of Comparative A to 181.92 grams of water and stirring the solution until blended. Comparative A is not a polyurethane mixture. The viscosities of these solutions were measured immediately and after 2 weeks at room temperature using a Brookfield LVT viscometer Table 7 shows the viscosities of these solutions.

TABLE 7

| Polyurethane and Zinc in Water* | Fresh Solution Viscosity, cps (spindle number) | 2 Weeks at Room Temperature Viscosity, cps (spindle number) |
|---|---|---|
| Example 1 | 49,900 (4) | Greater than 50000 (4) |
| Comparative A | 115 (2) | Separated |

*0.5% Zinc and 2% By Weight Solids Polyurethane in Water Brookfield Viscosity Measured at 12 RPM Table 7 shows that the polyurethane mixture of Example 1 was significantly better than Comparative A for thickening a 0.5% zinc solution in water.

c) Depilatories Containing Calcium Salts

Almost all depilatories use the calcium salt of thioglycolic acid as the active ingredient. The depilatories are thickened so the calcium salt does not settle out and to provide desired end-use viscosity.

A solution of 0.5% calcium and 2% by weight solids of the polyurethane mixture of Example 1 was made by adding 2.76 grams of calcium chloride and 20 grams of Example 1 (20% by weight solids) to 177.24 grams of water. The solution was stirred at room temperature. A solution of 0.5% by weight of calcium and 2% by weight solids of Comparative A (25% by weight solids) was made by adding 2.76 grams of calcium chloride and 16 grams of Comparative A to 181.24 grams of water and stirring the solution until blended. Comparative A is not a polyurethane mixture. The viscosities of these solutions were measured immediately at room temperature using a Brookfield LVT viscometer. Table 8 shows the viscosities of these solutions.

TABLE 8

| Polyurethane and Calcium in Water* | Viscosity, cps (Spindle Number) |
|---|---|
| Example 1 | 49,900 (4) |
| Comparative A | 316 (2) |

*0.5% Calcium and 2% By Weight Solids Polyurethane in Water Brookfield Viscosity Measured at 12 RPM Table 8 shows that the polyurethane mixture of Example 1 was significantly better than Comparative A for thickening a 0.5% calcium solution in water.

d) Shampoos Containing Sodium Salts

Salt tolerance is important for shampoos containing surfactants such as betaines. Salt tolerance is also important for many active ingredients in shampoos such as protein containing formulations. Shampoos are thickened to provide a desired end-use viscosity.

A solution of 1.0% by weight of sodium chloride and 2% by weight solids of the polyurethane mixture of Example 1 was made by adding 1.0 gram of sodium chloride and 10 grams of Example 1 (20% by weight solids) to 89 grams of water. The solution was stirred at room temperature. A solution of 1.0% by weight of sodium chloride and 2% by weight solids of Comparative A (25% by weight solids) was made by adding 1.0 gram of sodium chloride and 8 grams of Comparative A to 91 grams of water and stirring the solution until blended. Comparative A is not a polyurethane mixture. A solution of 1.0% by weight of sodium chloride and 2% by weight solids of Comparative B (20% by weight solids) was made by adding 1.0 gram of sodium chloride and 10 grams of Comparative B to 89 grams of water and stirring the solution until blended. Comparative B is a commercial polyurethane thickener which is not a polyurethane mixture. The viscosities of these solutions were measured initially and after 4 weeks at 40° C. using a Brookfield LVT viscometer. Table 9 shows the viscosities of these solutions.

TABLE 9

| Polyurethane and Salt in Water* | Fresh Solution Viscosity, cps (Spindle number) | 4 Weeks at 40° C. Viscosity, cps (Spindle number) |
|---|---|---|
| Example 1 | 48,500 (5) | 45,000 (5) |
| Comparative A | 700 (3) | 490 (3) |
| Comparative B | 10 (2) | Not Measured |

*1.0% Sodium Chloride and 2% By Weight Solids Polyurethane Brookfield Viscosity Measured at 12 RPM Table 9 shows that the polyurethane mixture of Example 1 was significantly better than Comparative A and Comparative B for thickening a 1.0% sodium chloride solution in water.

e) Facial Make-Up and Sunscreen containing pigments

Facial make-up such as, for example, eye shadow and face powder, contain high solids slurries of pigments, such as, for example, Kaolin clay and calcium carbonate. Sunscreens contain titanium dioxide and other microsized pigments. Facial make-up and sunscreens must be thickened in order to have the desirable consistency when applied to the skin.

A solution of 30% by weight of Kaolin clay and 1% by weight solids of the polyurethane mixture of Example 1 was made by adding 30 gram of Kaolin clay and 5 grams of Example 1 to 65 grams of water and stirring. A solution of 30% by weight of Kaolin clay and 1% by weight solids of Comparative A (25% by weight solids) was made by adding 30 grams of Kaolin clay and 4 grams of Comparative A to 66 grams of water and stirring the solution until blended. Comparative A is not a polyurethane mixture. A solution of 30% by weight of calcium carbonate and 1% by weight solids of Example 1 was made by adding 30 grams of calcium carbonate and 5 grams of Example 1 to 65 grams of water and stirring the solution until blended. A solution of 30% by weight of calcium carbonate and 1% by weight solids of Example A was made by adding 30 grams of calcium carbonate and 4 grams of Comparative A to 66 grams of water and stirring the solution until blended. The viscosities of these solutions were measured using a Brookfield LVT viscometer. Table 10 shows the viscosities of these solutions.

TABLE 10

| | Brookfield Viscosity 12 RPM (Spindle Number) | |
|---|---|---|
| Solution* | 30% Kaolin Clay | 30% Calcium Carbonate |
| Example 1 | 100,000 (5) | 60,000 (5) |
| Comparative A | 14,000 (4) | 3,400 (4) |

30% By weight pigment and 1.0% By Weight Solids Polyurethane

Table 10 shows that the polyurethane mixture of Example 1 was superior to Comparative A for thickening a 30% Kaolin Clay solution and a 30% Calcium Carbonate solution.

f) Hand Creams and Hand Lotions Containing Mineral Oil

Hand cream and lotion formulations containing mineral oil must be thickened to provide the desired consistency upon application. Mineral oil and water are immiscible and will separate on standing.

A solution of 10% by weight mineral oil and 2% by weight of the polyurethane mixture of Example 1 was made by adding 10 grams of mineral oil and 10 grams of Example 1 to 80 grams of water and stirring the solution until blended. A solution of 10% by weight mineral oil and 2% by weight of Comparative A was made by adding 10 grams of mineral oil and 8 grams of Comparative A to 88 grams of water and stirring the solution until blended. Comparative A is not a polyurethane mixture. The viscosities of these solutions were measured at room temperature using a Brookfield LVT viscometer. The results are shown in Table 11.

TABLE 11

| Polyurethane Solution* | Brookfield Viscosity 12 RPM (Spindle number) |
|---|---|
| Example 1 | Greater than 100,000 (5) |
| Comparative A | Separated |

*10% Mineral Oil and 2% By Weight Solids Polyurethane in Water

Table 11 shows that the polyurethane mixture of Example 1 was useful for thickening a 10% mineral oil solution and avoiding separation of the mineral oil solution.

EXAMPLE 19

Use of Polyurethane Mixture in Cleaners

Several cleaners contain acids as the active ingredients, such as, for example, metal cleaners, de-scalants, toilet bowl cleaners, household cleansers, automatic dishwash rinse additives, transportation cleaners, metal polishes, dairy cleaners, liquid abrasive cleaners, and the like. The acids must be compatible with the thickeners. These cleaning formulations must be thickened to obtain a desired end use viscosity.

A solution of 5% by weight phosphoric acid and 2% by weight solids of the polyurethane mixture of Example 1 was made by adding 5.88 grams of 85% phosphoric acid and 10 grams of Example 1 to 84.12 grams of water. A solution of 5% by weight sulfuric acid and 2% by weight solids of the polyurethane mixture of Example 1 was made by adding 5.21 grams of 96% sulfuric acid and 10 grams of Example 1 to 84.79 grams of water. A solution of 10% by weight citric acid and 2% by weight solids of the polyurethane mixture of Example 1 was made by adding 10 grams of citric acid and 10 grams of Example 1 to 80 grams of water. The viscosities of these solutions were measured initially and after 2 weeks at room temperature using a Brookfield LVT viscometer. The results are shown in Table 12.

TABLE 12

| | Brookfield Viscosity 12 RPM (Spindle number) | |
|---|---|---|
| Acid* | Initial Viscosity, cps | Viscosity after 2 Weeks at Room Temperature, cps |
| 5% Phosphoric | >100,000 (5) | >100,000 (5) |
| 5% Sulfuric | 37,000 (4) | 31,000 (4) |
| 10% Citric Acid | 12,250 (4) | 7,500 (4) |

*Acid Solutions and 2% By Weight Solids Polyurethane

Table 12 shows that the polyurethane mixture of Example 1 was useful for thickening acid solutions.

We claim:

1. A mixture of polyurethanes comprising a first polyurethane with at least two end groups, where each end group comprises a terminal isocyanate and a polyether; a second polyurethane with at least two end groups, where each end group comprises a terminal isocyanate group and a non-functional group; and a third polyurethane with at least two end groups, where one end group comprises a terminal isocyanate and a polyether and one other end group comprises a terminal isocyanate and a nonfunctional group.

2. An aqueous composition comprising from 0.005 to 20 percent by weight of the polyurethane mixture of claim 1.

3. A method of improving the sag resistance of an aqueous composition by adding the polurethane mixture of claim 1 to an aqueous composition at a concentration of from 0.005 to 20 percent by weight of the aqueous composition.

4. A method of increasing the viscosity of an aqueous composition by adding the polyurethane mixture of claim 1 to the aqueous composition at a concentration of from 0.005 to 20 percent by weight of the aqueous composition.

5. The polyurethane mixture of claim 1 where the polyether is an alkyl or aryl polyether alcohol.

6. The polyurethane mixture of claim 1 where the polyether is polyethylene glycol methyl ether or polypropylene glycol methyl ether.

7. The polyurethane mixture of claim 6 where the non-functional group is derived from 1-octadecanol.

8. The polyurethane mixture of claim 1 where each polyurethane in the mixture is present in an amount ranging from 5 to 90 mole percent.

9. The polyurethane mixture of claim 1 where the first polyurethane is present in the mixture in an amount ranging from about 8.3 to about 25 mole percent, the second polyurethane is present in the mixture in an amount ranging from about 25 to about 75 mole percent, and the third polyurethane is present in the mixture in an amount ranging from about 16.7 to about 50 mole percent.

10. The polyurethane mixture of claim 1 where the first polyurethane is present in the mixture in an amount ranging from about 12.5 to about 25 mole percent, the second polyurethane is present in the mixture in an amount ranging from about 25 to about 62.5 mole percent, and the third polyurethane is present in the mixture in an amount ranging from about 25 to about 50 mole percent.

11. A paint comprising the composition of claim 1.

12. A hair conditioner comprising the composition of claim 1.

13. A hair shampoo comprising the composition of claim 1.

14. An astringent comprising the composition of claim 1.

15. A depilatory comprising the composition of claim 1.

16. A sunscreen comprising the composition of claim 1.

17. A facial make-up comprising the composition of claim 1.

18. A hand cream or a hand lotion comprising the composition of claim 1.

19. A cleaner comprising the composition of claim 1.

20. A polyurethane comprising two end groups, where one end group comprises a terminal isocyanate and a polyether and one other end group comprises a terminal isocyanate and a non-functional group.

21. The polyurethane of claim 19 where the polyether is an alkyl or aryl polyether alcohol.

22. The polyurethane of claim 19 where the polyether is polyethylene glycol methyl ether or polypropylene glycol methyl ether.

23. The polyurethane of claim 19 where the non-functional group is derived from 1-octadecanol.

* * * * *